United States Patent [19]

Hill

[11] Patent Number: 4,545,980

[45] Date of Patent: Oct. 8, 1985

[54] ORGANOSILOXANES AND PREPARATION THEREOF

[75] Inventor: Michael P. Hill, Saint Lythans, Wales

[73] Assignee: Dow Corning Ltd., Barry, Wales

[21] Appl. No.: 707,340

[22] Filed: Mar. 1, 1985

[30] Foreign Application Priority Data

Mar. 5, 1984 [GB] United Kingdom ............... 8405731

[51] Int. Cl.$^4$ .............................. C07F 7/08; C07F 7/18
[52] U.S. Cl. ....................................... 424/60; 556/440
[58] Field of Search ........................... 556/440; 424/60

[56] References Cited

U.S. PATENT DOCUMENTS 3,427,337  2/1969  Miller et al. ..................... 556/440
3,746,734  7/1973  Berger et al. .................... 556/440
3,878,263  4/1975  Martin .......................... 556/440 X Primary Examiner—Paul F. Shaver
Attorney, Agent, or Firm—George A. Grindahl

[57] ABSTRACT

Process for preparing organosiloxanes having in the molecule at least one unit of the general formula

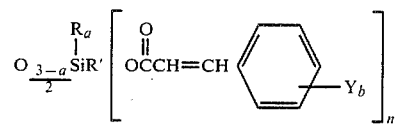

in which R is $C_{1-4}$ alkyl or a phenyl group, R' represents an aliphatic or aromatic group composed of carbon, hydrogen and optionally oxygen and having a valency of $n+1$, Y represents OH or alkoxy, a is 0, 1 or 2, b is 0 or 1 and n is 1, 2 or 3. The process comprises reacting an organosiloxane having silicon-bonded hydroxyalkyl or hydroxyaryl substituents with the appropriate acid chloride.

The organosiloxanes absorb ultra violet radiation and are useful as sunscreen agents.

Also claimed are certain novel siloxanes which can be obtained by the said process.

9 Claims, No Drawings

ORGANOSILOXANES AND PREPARATION THEREOF

This invention relates to a process for the preparation of organosiloxanes and is particularly concerned with the preparation of organosiloxanes which absorb ultra violet radiation and which are useful inter alia as sunscreen agents.

A number of organic compounds, generally organic carbonyl compounds, are known which have the property of absorbing ultra-violet radiation. Such compounds have found application in the preparation of sunscreen compositions which function to reduce the harmful effects which can arise from exposure to U.V. radiation. Although such materials provide an adequate protective effect they are generally easily removed from the substrate to which they have been applied. In particular cosmetic sunscreen preparations can be removed from the skin during bathing thus requiring repeated applications if protection is to be maintained. Also it would be desirable for the active ingredient to remain on the surface of the skin rather than be absorbed thereby.

U.S. Pat. Nos. 3,068,152 and 3,068,153 disclose sunburn preventive compositions comprising an inert, non-toxic, non U.V.-light absorbing carrier having dispersed therein respectively an organosilicon compound containing at least one silicon-bonded phenylcarbamylalkyl group or at least one silicon-bonded acylaminoalkyl group. Such products are, however, considered to be less desirable for cosmetic applications than those which are free of nitrogen in the molecule. British Pat. No. 1 164 522 discloses nitrogen-free organosilicon compounds which are useful as sunscreen agents and which may be prepared by the reaction of allyl cinnamate with an organosiloxane having silicon-bonded hydrogen atoms in the molecule. However, due to the occurrence of secondary rearrangement reactions the yield of desired product is generally poor. A method of preparing organosilicon cinnamates which avoids such secondary reactions is described in British Pat. No. 1 373 458. The said method involves the reaction of allyl cinnamate with a silane or siloxane containing mercaptoalkyl groups. The products can, however, retain some residual odour from the mercaptoalkyl starting materials thus rendering them unsuitable for certain cosmetic applications.

According to the present invention there is provided a process for the preparation of an organosiloxane having in the molecule at least one unit of the general formula

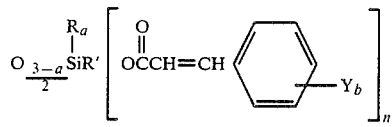

wherein R represents an alkyl group having from 1 to 4 inclusive carbon atoms or a phenyl group, R' represents an aliphatic or aromatic group having a valency of $n+1$ and being composed of carbon and hydrogen or of carbon, hydrogen and oxygen wherein the oxygen is present in the form of ether linkages or in hydroxyl groups, Y when present represents a hydroxyl group or an alkoxy group, having from 1 to 4 carbon atoms, a has a value of 0, 1 or 2, b is 0 or 1 and n is 1, 2 or 3, said process comprising reacting together (A) an organosiloxane having in the molecule at least one unit of the general formula

any remaining units in the organosiloxane having the general formula

wherein R and a are as hereinabove defined, G represents a monovalent aliphatic or aromatic group composed of carbon, hydrogen and, optionally, oxygen in the form of ether linkages and having substituted therein at least one alcoholic or phenolic hydroxyl group, Q represents a monovalent hydrocarbon group or a monovalent halogenated hydrocarbon group and d is 0, 1, 2 or 3, and (B) a compound having the general formula

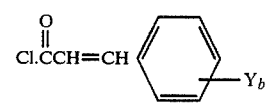

Y and b being as hereinabove defined.

The organosiloxanes prepared according to the process of this invention have in the molecule at least one unit of the general formula (I), any other units being those represented by the general formula (III) as defined herein. In the unit general formulae R, when present, may be methyl, ethyl, propyl, butyl or phenyl but is preferably methyl. The group R' has a valency of $n+1$ and may be composed of carbon and hydrogen or of carbon, hydrogen and oxygen wherein the oxygen is present in an ether linkage or in a hydroxyl group. Examples of R' groups therefore include $-(CH_2)_3-$, $-(CH_2)_4-$, $-CH_2CH.CH_3CH_2-$, $-CH_2CH_2C(CH_3)_2-$, $-CH_2CH_2C(CH_3)_2(CH_2)_3-$,

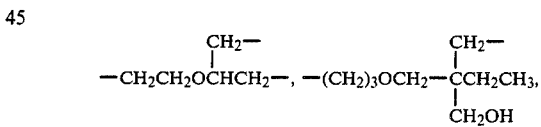

$-(CH_2)_3OCH_2CHCH_2-$, $-(CH_2)_3O(CH_2)_3-$ and $-CH_2CH_2C_6H_4-$. The substituent Y, when present (b=1), is $-OH$ or an alkoxy group having from 1 to 4 inclusive carbon atoms, and is preferably a methoxy group.

In the general formula of siloxane units (III) Q represents a monovalent hydrocarbon group, or a monovalent halogenated hydrocarbon group, for example alkyl e.g. methyl, ethyl, propyl, octyl and 2,4,4-trimethylpentyl, alkenyl e.g. vinyl, aryl e.g. phenyl, aralkyl e.g. benzyl and 2-phenylethyl, and fluoroalkyl e.g. 3.3.3-trifluoropropyl. Preferably Q has less than 8 carbon atoms and is most preferably the methyl group.

Reactant (A) employed in the process of this invention is an organosiloxane having at least one unit of the general formula (II) any remaining units being those of the general formula (III). For most applications it is preferred to employ as reactant (A) polydiorganosiloxanes, especially siloxane copolymers composed of units (II), wherein a is 1 or 2, and units (III) wherein d is 2 or 3. For example, the preferred organosiloxanes (A) may be composed of one or more units (II) wherein a is 2 in combination with units (III) wherein d is 2. Or the organosiloxane may consist of units (II) wherein a is 1 in combination with units (III) wherein d is 2 and units (III) wherein d is 3. The substituent G present in (II) may be for example —(CH$_2$)$_3$OH, —CH$_2$CHCH$_3$CH$_2$OH, —CH$_2$CH$_2$C(CH$_3$)$_2$OH, —CH$_2$CH$_2$CCH$_3$(OH)C$_2$H$_5$, —(CH$_2$)$_3$O(CH$_2$)$_3$OH, —(CH$_2$)$_3$OCH$_2$CH(OH)CH$_2$OH, —(CH$_2$)$_3$OCH$_2$(CH$_2$OH)$_2$C.CH$_2$CH$_3$, —(CH$_2$)$_2$CH.(CH$_2$OH)$_2$ and —CH$_2$CH$_2$C$_6$H$_4$OH. Organosiloxanes (A) are known materials and may be prepared by the reaction of an organosiloxane having silicon-bonded hydrogen atoms with an unsaturated alcohol in the presence of a platinum catalyst. Such a reaction wherein the unsaturated alcohol is, for example, trimethylolpropane-monoallyl ether is disclosed in British Pat. No. 998 549. Examples of other unsaturated alcohols which may be employed are allyl alcohol, methallyl alcohol, allyloxy propanol, allyloxy glycerol, 3-hydroxy-3-methyl-1-butene, 3-hydroxy-3,5-dimethyl-1-hexene and 1-vinyl-4-hydroxybenzene. Preferred as reactant (A) are hydroxyalkyl organosiloxanes derived from 3-hydroxy-3-methyl-1-butene, that is organosiloxanes wherein G represents the group —CH$_2$CH$_2$C(CH$_3$)$_2$OH. Organosiloxanes prepared from such hydroxyalkyl siloxanes are novel substances. Therefore, according to another aspect of the invention there are provided organosiloxanes having in the molecule at least one unit of the general formula

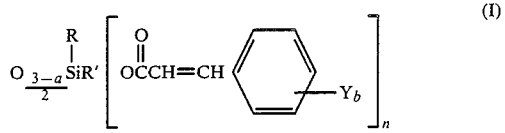
(I)

any remaining units in the organosiloxane having the general formula

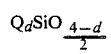

wherein R, Y, Q, a, b, d and n are as defined in Claim 1 and R' represents the group —CH$_2$CH$_2$C(CH$_3$)$_2$—.

Reactants (B) employed in the process of this invention are certain acid chlorides for example cinnamoyl chloride and p-methoxy cinnamoyl chloride.

The reaction between (A) and (B) according to the process of this invention is preferably carried out in the presence of an acceptor for the HCl by-product. Any of the known HCl acceptors may be employed including, for example, triethylamine, diethylamine, dimethylaniline and pyridine, provided they are unreactive with respect to (A) and (B). It is also preferred to employ phase transfer catalysts for the reaction e.g. quaternary ammonium salts or certain polyglycols.

If desired the process of this invention can be conducted in the presence of one or more solvents for the reactants. Suitable solvents include for example hexane, toluene, petroleum ether, xylene and clhorinated hydrocarbons. Depending on the specific reactants present the reaction between (A) and (B) can be carried out at temperatures ranging from below normal ambient temperature i.e. below about 20° C. up to the reflux temperature of the reaction mixture. In general it is preferred that the reactants are maintained at a temperature within the range from about 30° C. to about 120° C.

The relative amounts of the reactants (A) and (B) employed in the process of this invention are not narrowly critical and will depend generally upon the proportion of available hydroxyl groups to be reacted. Preferably reactant (B) is employed in an amount of at least one mole per alcoholic or phenolic hydroxyl group in organosiloxane (A). Less than stoichiometric proportions may, however, be used where residual hydroxyl groups are desired in the product.

The organosiloxanes prepared according to this invention may vary in molecular size from the disiloxanes to high molecular weight homopolymers and copolymers and may range in consistency from freely-flowing liquids to resinous solids. Preferred for cosmetic applications are the liquid, substantially linear polydiorganosiloxane homopolymers and copolymers. The organosiloxanes absorb ultra-violet radiation and are therefore useful as agents for preventing sunburn. They may be applied per se to the skin but are more preferably formulated into compositions with, for example, ethanol, glycerine, mineral oil and cream base materials such as stearic acid, propylene glycol, beeswax and cetyl alcohol. Other conventional ingredients e.g. perfumes and known U.V.-absorbing substances may also be included in the formulated compositions. The organosiloxanes prepared according to this invention are also useful in the coating of substrates e.g. wood, plastics or metals, either per se or as additions to coating compositions.

The following examples, in which the parts are expressed by weight and Me represents the methyl group, illustrate the invention.

EXAMPLE 1

600 g of a copolymer having the average formula

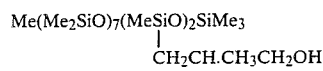

and a hydroxyl content of 4.46% by weight was charged to a flask with triethylamine (173 g) and hexane (380 g) maintained under nitrogen. A solution of p-methoxycinnamoyl chloride (336 g) in hexane (202 g) at 60° C. under nitrogen was then slowly added to the flask. During the addition the temperature of the reaction mixture in the flask rose to 67° C. The contents of the flask were then refluxed for 40 minutes. At the end of this period the reaction mixture was cooled and water added slowly to hydrolyse any excess acid chloride. The resulting mixture was filtered and allowed to separate in a separating funnel.

The oil phase was recovered and the hexane present therein removed by distillation under reduced pressure the final temperature/pressure being 148° C./8 mm.Hg. The product was a pale yellow oil having a viscosity of 644cS at 25° C., an extinction coefficient (1% solution in CH$_2$Cl$_2$) of 404 and λ max of 310 nm.

EXAMPLE 2

Employing a procedure similar to that described in Example 1 a similar methylsiloxane copolymer, except that it had a measured hydroxyl content of 5.26%, was reacted with cinnamoyl chloride. In this experiment 1 mole of cinnamoyl chloride and 1 mole of triethylamine were employed per mole of OH in the methylsiloxane.

The product was a pale yellow oil having a viscosity of 288 cS, extinction coefficient (1% solution in $CH_2Cl_2$) of 433 and λ max of 276 nm.

EXAMPLE 3

The hydroxyalkyl siloxane reactant employed in this Example had the average formula

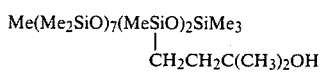

contained 3.69% by weight of OH and was prepared by the platinum catalysed reaction of a siloxane having silicon-bonded hydrogen atoms and 3-hydroxy-3-methyl-1-butene.

Into a reaction flask under a positive pressure of dry nitrogen were placed 80 g of analytical purity toluene and 42.7 g (0.217 mole) of molten p-methoxycinnamoyl chloride. The temperature of the flask was raised to 100° C. and the mixture became clear and homogeneous. To the flask was then added during a period of 60 minutes a mixture of 21.9 g (0.217 mole) of dry triethylamine, 20 g of analytical purity toluene and 100 g of the hydroxyalkyl siloxane. The flask and contents was then maintained at 110° C. for a further 5 hours, allowed to cool to 20° C. and the amine hydrochloride by-product removed by washing with water.

The organic layer was recovered and heated at 150° C./10 mbar to remove the toluene. The product was a red-brown liquid having a viscosity of $5.46 \times 10^{-4} m^2/s$ and the average formula

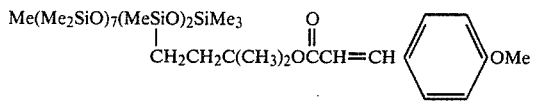

Measurement of the extinction coefficient (1% solution in $CH_2Cl_2$) and λ max yielded values of 404 and 310 nm respectively.

EXAMPLE 4

The hydroxyalkyl siloxane reactant employed in this Example had the average formula

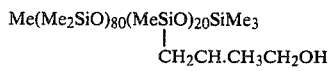

and a measured OH content of 2.62% by weight. It was prepared by the platinum catalysed addition of methallyl alcohol to a polydimethylsiloxane having silicon-bonded hydrogen atoms.

Into a reaction flask were placed 66.1 g (0.655 mole) of triethylamine, 385 g of analytical purity hexane and 116.7 g (0.594 mole) of molten p-methoxycinnamoyl chloride. This mixture was then heated to about 55° C. at which point the acid chloride dispersed and the mixture was a mobile liquid. To the mixture was then added 385 g of the hydroxyalkyl siloxane dropwise over a period of about 40 minutes. The mixture was held at about 55° C. until the addition of siloxane was complete and then heated to vigorous reflux for a further 30 minutes. It was then allowed to cool and the amine hydrochloride removed by washing with water.

The organic phase was recovered as a viscous, cloudy liquid and was washed with 50 g of an aqueous solution of sodium bicarbonate (10 g). After the addition of additional water and hexane to assist separation of the aqueous and organic phases the organic phase was recovered, filtered and to it was added 156 g of isopropyl myristate. This mixture was then heated under vacuum (110° C./10 mbar) to remove hexane and leave a product which was an approximately 70% by weight solution of the desired siloxane polymer in isopropyl myristate. This product had a viscosity of $3.75 \times 10^{-4} m^2/s$, was of an orange colour and exhibited an extinction coefficient (1% in $CH_2Cl_2$) of 229.

EXAMPLE 5

The hydroxyalkyl siloxane reactant employed in this Example was the same as that employed according to Example 3 except that the measured OH content was 3.60% by weight.

Into a reaction flask which had been purged with dry nitrogen was placed 19.65 g of molten p-methoxycinnamoyl chloride, 40 ml of analytical purity hexane and 0.8 g of a methyltrialkyl ($C_8$-$C_{10}$) ammonium chloride. The reaction mixture was heated to reflux (65° C.) and there was added to it over a period of 20 minutes 10 ml of dry hexane, 10.1 g of triethylamine and 50 g of the hydroxyalkyl siloxane. On completion of the addition a precipitate formed and the mixture was maintained at reflux (70° C.) for 5 hours. When the reaction mixture had cooled to 23° C. 200 g water and 50 g hexane were added. The aqueous phase was separated from the organic phase and the latter filtered and stripped of solvent at 120° C. and $8 \times 10^2$ Pa. The product remaining was a siloxane polymer having the same average structure as the product of Example 3.

| Viscosity | $2.37 \times 10^{-4} m^2/s$ |
|---|---|
| Extinction coefficient | 20,598 |
| Extinction coefficient (1% in $CH_2Cl_2$) | 310.9 |

That which is claimed is:

1. A process for the preparation of an organosiloxane having in the molecule at least one unit of the general formula

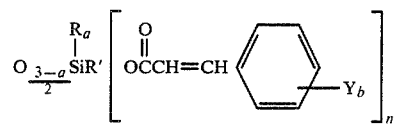

wherein R represents an alkyl group having from 1 to 4 inclusive carbon atoms or a phenyl group, R' represents an aliphatic or aromatic group having a valency of n+1 and being composed of carbon and hydrogen or of carbon, hydrogen and oxygen wherein the oxygen is present in the form of ether linkages or in hydroxyl groups, Y when present represents a hydroxyl group or an alkoxy group having from 1 to 4 carbon atoms, a has a value of 0, 1 or 2, b is 0 or 1 and n is 1, 2 or 3, said process comprising reacting together (A) an organosiloxane having in the molecule at least one unit of the general formula

any remaining units in the organosiloxane having the general formula

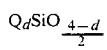

wherein R and a are as hereinabove defined, G represents a monovalent aliphatic or aromatic group composed of carbon, hydrogen and, optionally, oxygen in the form of ether linkages and having substituted therein at least one alcoholic or phenolic hydroxyl group, Q represents a monovalent hydrocarbon group and d is 0, 1, 2 or 3, and (B) a compound having the general formula

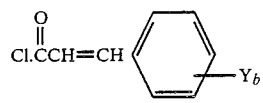

Y and b being as hereinabove defined.

2. A process as claimed in claim 1 wherein b is 1 and Y represents the methoxy group.

3. A process as claimed in claim 1 wherein G represents the group —$CH_2CH_2C(CH_3)_2OH$.

4. A process as claimed in claim 1 wherein the organosiloxane (A) is a polydiorganosiloxane.

5. A process as claimed in claim 1 wherein the reaction is carried out in the presence of a phase transfer catalyst.

6. Organosiloxanes having in the molecule at least one unit of the general formula

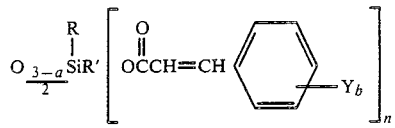

any remaining units having the general formula

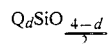

wherein R, Y, Q, a, b, d and n are as defined in claim 1 and R' represents the group —$CH_2CH_2C(CH_3)_2$—.

7. Organosiloxanes as claimed in claim 6 wherein b is 1 and Y represents the methoxy group.

8. A sunscreen composition containing an organosiloxane which has been produced according to the process claimed in claim 1.

9. A sunscreen composition containing an organosiloxane as claimed in claim 6.

* * * * *